(12) United States Patent
Bohner

(10) Patent No.: US 7,393,405 B2
(45) Date of Patent: Jul. 1, 2008

(54) HYDRAULIC CEMENT BASED ON CALCIUM PHOSPHATE FOR SURGICAL USE

(75) Inventor: Marc Bohner, Aarau (CH)

(73) Assignee: H.C. Robert Mathys Stiftung, Bettlach (CH)

( * ) Notice: Subject to any disclaimer, the term of this patent is extended or adjusted under 35 U.S.C. 154(b) by 311 days.

(21) Appl. No.: 10/517,166

(22) PCT Filed: May 13, 2003

(86) PCT No.: PCT/CH03/00304

§ 371 (c)(1), (2), (4) Date: Dec. 7, 2004

(87) PCT Pub. No.: WO04/000374

PCT Pub. Date: Dec. 31, 2003

(65) Prior Publication Data

US 2005/0241535 A1    Nov. 3, 2005

(30) Foreign Application Priority Data

Jun. 19, 2002 (WO) ............... PCT/CH02/00332

(51) Int. Cl.
*A61F 2/28* (2006.01)
*C04B 12/02* (2006.01)

(52) U.S. Cl. ............. 106/690; 106/691; 623/23.62; 623/23.61; 623/23.56; 424/602

(58) Field of Classification Search ........ 424/602; 623/23.62, 23.61, 23.56; 106/690, 691
See application file for complete search history.

(56) References Cited

U.S. PATENT DOCUMENTS

| 4,518,430 A | 5/1985 | Brown et al. |
| 4,619,655 A | 10/1986 | Hanker et al. |
| 4,880,610 A | 11/1989 | Constantz |
| 5,338,356 A | 8/1994 | Hirano et al. |
| 5,605,713 A | 2/1997 | Boltong |
| 5,954,867 A | 9/1999 | Chow et al. |
| 6,206,957 B1 | 3/2001 | Driessens et al. |

FOREIGN PATENT DOCUMENTS

| JP | 2000-159564 | * 6/2000 |
| WO | WO 01/41824 | * 6/2001 |
| WO | WO 02/087649 | * 11/2002 |

OTHER PUBLICATIONS

WO 91/00252, Calcium Sulfate Hemihydrate Composition Having Utility in the Presence of Blood, Publication Date: Jan. 10, 1991.
WO 02/05861, A Composition for an Injectable Bone Mineral Substitute Material, Publication Date: Jan. 24, 2002.
Mirichi A A et al: "Calcium Phosphate Cements: Action of Setting Regulators on the Properties of the -Tricalcium Phosphate-Monoalcium Phosphate Cements" Biomaterials, . . . .
Nilsson M, Fernández E, Sarda S, Lidgren L, Planell JA., Characterization of a novel calcium phosphate/sulphate bone cement, Journal of Biomedical Materials Research (2002); pp. 600-607, vol. 61, Wiley Periodicals, Inc.

* cited by examiner

*Primary Examiner*—C. Melissa Koslow
(74) *Attorney, Agent, or Firm*—Rankin, Hill & Clark LLP

(57) ABSTRACT

A hydraulic cement is based on calcium phosphate for surgical use, and includes three components. The first component includes α-tricalcium phosphate powder particles. The second, component includes calcium sulphate dehydrate. The third component includes water. Furthermore the hydraulic cement does not contain more calcium sulfate hemihydrate (CSH) than 10% of the total amount of the calcium sulphate dihydrate (CSD).

51 Claims, No Drawings

HYDRAULIC CEMENT BASED ON CALCIUM PHOSPHATE FOR SURGICAL USE

This invention concerns a hydraulic cement based on calcium phosphate for surgical use.

Calcium phosphate cements (CPC) are mixtures of one or several calcium phosphate powders that react with water to form a new calcium phosphate compound, generally an apatite. Through these chemical reactions, there is hardening of the aqueous paste. In vivo studies have shown that CPC are generally biocompatible, osteoconductive and somehow bioresorbable. Therefore, CPC have been the subject of a large and growing interest of the medical community. Several products have been introduced on the market. However, all of these products have some drawbacks From the U.S. Pat. No. 4,880,610 a mixture of an aqueous solution, α-tricalcium phosphate (α-TCP; $Ca_3(PO_4)_2$), monocalcium phosphate monohydrate (MCPM; $Ca(H_2PO_4)_2 \cdot H_2O$), and calcium carbonate (CC; $CaCO_3$) is known. Due to the presence of MCPM, the paste is initially acid. Therefore, dicalcium phosphate dehydrate (DCPD; $CaHPO_4 \cdot 2H_2O$) crystals form during the initial seconds of the setting reaction, hence rendering the paste hard. These crystals have to be broken down to be able to keep a paste consistency and to be able to fill the bone defect with the cement paste. Hardening of the paste occurs in a second step via the formation of carbonated apatite. Due to the fact that the paste hardens in two steps, the cement cannot be mixed with a pestle and a spatula: it requires the use of a mixing machine providing large mechanical forces (to break DCPD crystals). For the surgeon, this is obviously a disadvantage.

From the U.S. Pat. No. 5,338,356 a mixture of an aqueous solution, α-TCP, tetracalcium phosphate (TTCP; $Ca_4(PO_4)_2O$), dicalcium phosphate (DCP; $CaHPO_4$) and hydroxyapatite (HA, $Ca_5(PO_4)_3OH$) is known. This paste sets via one single setting reaction to form an apatite. As a result, the mixing procedure is very simple. However, the presence of a very basic calcium phosphate (TTCP) decreases the bioresorbability of the set cement [4], which might be undesirable. Additionally, the cement formulation is rather complicated with its four different powder components.

From the U.S. Pat. No. 4,518,430 a mixture of an aqueous solution, TTCP and DCP is known. As for the cement according to U.S. Pat. No. 5,338,356, the use of a basic calcium phosphate (TTCP) reduces the bioresorbability of the cement. Moreover, the setting reaction is slow and must occur in the absence of blood flow.

From U.S. Pat. No. 4,619,655 it is known to use plaster of Paris (=calcium sulphate hemihydrate, CSH; $CaSO_4 \cdot 1/2H_2O$) in combination with a calcium phosphate ceramic, such as a "calcium triphosphate". However, these mixtures do not contain CSD. Additionally, the calcium phosphate ceramic is not added as a powder but as particles. Particles larger than 20 µm are not reactive enough. Therefore, the setting reaction that could result from the hydrolysis of α-tricalcium phosphate particles would take a few hours which is far too long for a medical use.

From U.S. Pat. No. 5,605,713 a mixture of "three to four calcium phosphates", in particular α-TCP is known, but none of the mentioned calcium compounds is CSD.

From U.S. Pat. No. 5,954,867 a method is known for "making a calcium phosphate cement which self-sets at ambient temperatures comprising combining a calcium phosphate salt which is substantially free of TTCP with an additional source of calcium and an aqueous solution adjusted with a base to maintain a pH of about 12.5 or above". Such a high basic pH-value is not desirable due to the adverse effect on the tissue cells which leads to a low compatibility of such a cement.

From U.S. Pat. No. 6,206,957 a "biocement paste comprising (a) tricalcium phosphate (b) at least one further calcium phosphate-containing compound, (c) a cohesion promoter and (d) a setting accelerator, wherein components (a) and (b) form a cement powder, and components (c) and (d) are in an aqueous solution, wherein said cement powders . . . " is known. In this patent, not only one, but two calcium phosphate compounds were used, one being α-TCP. However, no mention of CSD is made.

In the scientific literature, Nilsson et al. (Key Eng. Mater, vols. 218-220 (2202) pp 365-368) described the effects of mixing α-TCP with CSH. But again, the use of CSD is not mentioned. Although some of the CSH is hydrolysed in CSD in the presence of water so that entanglement of CSD crystals can take place this reaction has to compete with a second reaction taking place simultaneously and which is the hydrolysis of α-TCP and entanglement of apatite crystals. The occurrence of two competing parallel reactions complicates the setting reaction and leads to interactions between the two competing setting reactions, hence leading to inadequate rheological properties of the cement paste. "Inadequate" meaning that the paste requires more water to be a paste, which has a negative effect on the injectability of the cement paste and the final mechanical properties of the cement.

From WO02/05861 LIDGREN a cement composition is known which is based on an aqueous liquid, calcium sulfate hemihydrate (CSH) as a first reaction component, calcium phosphate as a second reaction component and an accelerator for the reaction of CSH with water. Therefore, as with the mixture of Nilsson, there are two simultaneous setting reactions taking place, namely the hydrolysis of CSH and of the calcium phosphate, which leads to inadequate rheological properties of the cement paste (bad injectability) and a hardened cement with poor mechanical properties.

It would be desirable therefore to provide a calcium phosphate cement which overcomes or alleviates in part or all of the above mentioned drawbacks.

According to a broad aspect, the present invention solves the problem of providing a hydraulic cement based on calcium phosphate for surgical use which has not a very basic component such as TTCP, consists of a limited amount of components, sets fast, and is easy to mix.

CSH has a solubility roughly 10 times larger than that of CSD. Therefore, small amounts of CSH can have a very large impact on the cement. It is therefore very important to limit the CSH amount to a minimum, namely at least 10 times lower than the CSD amount. But it is preferable to lower this amount down to 1-2% and more preferably to 0%. Thus, a hydraulic cement according to the invention does not contain more calcium sulfate hemihydrate (CSH) than 10% of a total amount of said calcium sulphate dihydrate (CSD). Preferably, the amount of calcium sulfate sulfate hemihydrate (CSH) of the cement is lower than 5%, or more preferably 2%, of said calcium sulphate dihydrate (CSD).

The cement according to the invention comprises a first component comprising α-TCP powder particles, a second component comprising calcium sulphate dihydrate (CSD; $CaSO_4 \cdot 2H_2O$) and a third component comprising water. α-TCP acts as the setting component whereas CSD is simultaneously a lubricant and enables an adequate control of the Ca/P molar ratio. In one embodiment, the cement consists of a powder/liquid formulation to be mixed, whereby (a) a powder comprises said first and second component, and (b) a liquid comprises the third component. Component (a) can additionally comprise water-soluble phosphate salts, and component (b) can comprise a polymer. In another embodiment, the cement consists of a powder comprising said first and second component, a first viscous solution comprising said third component, and a second solution comprising a contrasting agent.

CSD is a very biocompatible material. It is obtained by mixing CSH with water. CSD has a solubility in water close to 10 mM (in calcium ions), i.e. much larger than the concentration of calcium ions in the body. As a result, CSD implanted in a human body disappears by passive dissolution. However, as CSD is much more soluble than the solubility of hydroxyapatite, and as the body contains a large amount of phosphate ions, hydroxyapatite can precipitate around CSD implants. Precipitation can be enhanced if hydroxyapatite crystals are already present around CSD crystals. In the compositions described in this patent, α-TCP is transformed in an apatitic compound. CSD crystals can therefore be transformed into hydroxyapatite:

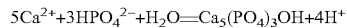

$$5Ca^{2+}+3HPO_4^{2-}+H_2O=Ca_5(PO_4)_3OH+4H^+$$

As a result, α-TCP/CSD mixtures implanted in vivo becomes denser and stronger with the implantation time, until all CSD is dissolved. Additionally, the precipitation of hydroxyapatite provokes a slight acidification of the cement surroundings, which is positive to keep a high bioresorbability.

Solubility data shows that the equilibrium pH between CSD and hydroxyapatite is close to pH 4. Therefore, if the cement was placed in pure water, the equilibrium pH should tend towards this pH value. In vivo, the pH value in the cement pores will always tend to decrease to reach this low equilibrium pH value. However, the body fluids are buffered at a pH value close to 7.4. Therefore, there will always be a competition between the latter two reactions: (a) acidification of the cement to reach equilibrium and (b) buffering of the cement by body fluids.

The use of CSD has also the advantage to promote the flow properties of the cement paste. This improvement is characterised by the fact that the amount of mixing liquid can be reduced when the amount of CSD is increased.

Preferably, in cement according to the invention, the first and second components are in the form of particles having an average diameter larger than 0.1 µm. In a preferred embodiment the powder particles of said first component have an average diameter inferior to 20 µm and preferably inferior to 10 µm. Typically the average particle diameter is chosen to be 1 µm. The specific surface area (SSA) of the powder particles of said first component is in the range of 0.05 to 10.000 m²/g, or more preferably within the range of 1 to 2 m²/g.

The setting time of the cement is an important property of the cement. If the setting time is too fast, the surgeon does not have time to use the cement before it is hard. If the setting time is too long, the surgeon must wait until he/she can close the wound. Therefore, an intermediate setting time is desirable. Values comprised between 1 and 20 minutes are in a good range. Preferable values are in the range of 2 to 15 minutes, in more details in the range of 5 to 12 minutes. Thus a setting time of a cement paste according to the invention, which is obtained by mixing a first component comprising α-tricalcium phosphate powder particles, a second component comprising calcium sulphate dihydrate (CSD) and a third component comprising water at 37° C., is between 1 and 20 minutes, or preferably between 2 and 15 minutes, or more preferably between 5 and 12 minutes.

In a preferred embodiment at least one of the three cement components comprises a setting regulator; a setting regulator being either a setting accelerator or a setting retarder.

The setting time can be controlled by the particle size of the α-TCP powder: the smaller the particle size, the faster the setting reaction. However, a decrease of the particle size can be difficult to achieve (especially for diameters below 1 µm). Therefore, other methods should be considered. A very efficient way to accelerate the setting time is to have large concentrations of phosphate ions in the mixing solution. This can happen via two ways: (i) a soluble phosphate salt is added as a powder in the cement formulation. Upon contact with the mixing solution, the phosphate salt dissolves, and hence accelerate the chemical reaction (LeChatelier principle). (ii) a soluble phosphate salt is pre-dissolved in the mixing liquid. Examples of soluble phosphate salts are $Na_2HPO_4$, $NaH_2PO_4$, $K_2HPO_4$, $KH_2PO_4$, $NH_4H_2PO_4$. Typical concentrations in the mixing liquid are in the range of 0.05 to 1.00 M. Another way to accelerate the setting reaction is to add nuclei for apatite crystal growth, as the nucleation step of the setting reaction is a limiting factor. Typically, apatite crystals can be used, preferably a calcium-deficient hydroxyapatite or hydroxyapatite powder. Small amounts (a few weight percents) are sufficient to drastically reduce the setting time.

When the setting time is too short, various setting additives can be added to increase the setting time. Typical examples are compounds which inhibits the nucleation and/or growth of apatite crystals. Common examples are pyrophosphate, citrate, or magnesium ions. One particularly interesting compound is calcium carbonate (CC; $CaCO_3$). Carbonate ions are present in human bone. Additionally, carbonate ions are able to reduce the size of apatite crystals, probably via the inhibition of apatite crystal growth.

The Ca/P molar ratio of α-TCP is 1.5. Any addition of CSD will lead to an increase of the global Ca/P molar ratio. Simultaneously, an addition of CSD will allow an additional precipitation of apatite, hence leading to larger mechanical properties, and lower porosity. It is well-known that the bioresorbability of calcium phosphate cements depends on the Ca/P molar ratio: an increase of the Ca/P molar ratio leads to a decrease of the bioresorption rate. Therefore, the resorbability of the cement can be controlled by the fraction of CSD used in the cement composition. For a low resorbability, a Ca/P molar ratio larger than 2 is ideal. Thus, in a cement according to the invention, the Ca/P molar ratio of the cement is greater than 1.5. Preferably the Ca/P molar ration of a cement according to the invention is greater than or equal to 1.667, and more preferably is greater than or equal to 2.0.

In recent years, the occurrence of osteoporotic fractures has dramatically increased. Considering the lack of adequate cure and the increasing number of elderly people, this trend is expected to continue. Osteoporotic fractures are often very difficult to repair, because the bone is very weak. It is therefore not possible to insert screws to hold osteosynthesis plates. A way to solve the problem is to inject a calcium phosphate cement into the osteoporotic bone to reinforce it. In order to prevent any extravasation of the cement into the tissues surrounding bone, it is very important to visualise the cement. The easiest way is to increase the radio-opacity of the cement, for example by means of contrasting agents. Metallic powders of tantalum, titanium or tungsten (among others) can be used. However, it might not be desirable to use such powders in partially bioresorbable cements. It is preferable to use liquid agents, such as iodine compounds. Examples are iopamidol, iohexol and iotrolan.

The injection of a CPC into an osteoporotic bone is only possible if the cement is well injectable. Often, CPC are not well injectable. The reason is a too large average particle size and a too low viscosity of the mixing liquid, leading to so-called filter pressing: when a pressure is applied on the cement paste (e.g. during cement injection), the liquid and solid phases are separated. The easiest way to solve the problem is to increase the viscosity of the mixing liquid, for example by adding small amounts of polysaccharides into the mixing liquid. Typical polymers that can be used are polysaccharide derivatives comprising hyaluronic acid or salt, chondroitin sulphate, dermantan sulphate, heparan sulphate, heparin, dextran, alginate, keratan sulphate, hydroxypropylmethyl cellulose, chitosan, xanthan gum, guar gum, carrageenan. The most interesting compounds are those already certified for medical applications, such as hyaluronate compounds. Typical concentrations are around 1% w/w. The additive used to control the cement rheology can be added to any one of said three components used to form the cement, and can be added in an amount that is larger that 1 weight percent (w/w) of the third component.

The viscosity of the mixing liquid is (as seen above) important to prevent filter-pressing. The viscosity of the cement paste is also a very important factor. The cement viscosity should be high enough to prevent a too fast mix with body fluids, such as blood. A mix with body fluids could prevent cement setting and hence lead to complications. The paste viscosity is also very important to prevent cement extravasation during bone augmentation (injection of cement into bone): the larger the viscosity, the lower the risk of extravasation. Therefore, the cement viscosity should be larger than 1 Pa·s at a shear rate of $400s^{-1}$, one minute after the start of cement mixing, and preferably above 10 or even 100 Pa·s at a shear rate of $400s^{-1}$, one minute after the start of cement mixing.

The viscosity of the cement paste depends obviously on the powder-to-liquid (P/L) ratio. An increase of the P/L ratio leads to a increase of the cement viscosity. If the P/L ratio is too high, the amount of mixing liquid is too low to fill up all the pores between the different solid particles, and hence to form a cement paste. The volume of mixing liquid (VL) should be in the range of: 0.5 VT<VL<10 VT where VT is the powder volume of the cement paste. More typical values are in the range of 1.0 VT<VL<2.5VT. By volume is meant the real volume (and not the apparent volume), i.e. the weight divided by the density of the material.

CPC particles have the disadvantage that they do not have macropores, i.e. pores larger than 50-100 μm in diameter, in which blood vessels and bone cells can grow in. As a result, the bioresorption occurs layer-by-layer and not everywhere in the cement bulk. To prevent this, bioresorbable or biodegradable granules made of calcium phosphate, CSD, polymer or bioglass whose diameter are at least two times larger than the average diameter of the powder particles of the first component can be added to the first or second component of the cement paste according to the invention. Upon implantation, the granules will dissolve, hence leaving empty pores. Typically, these granules, e.g. CSD granules, should have an average size in the range of 100 to 500 μm, or more preferably, in the range of 200 μm to 350 μm.

A different way to create macropores in the cement structure is to incorporate gas bubbles in the cement paste. This incorporation can be promoted by adding a tensioactive agent. Tensioactive agents can also be used to incorporate a poorly water-soluble contrasting agent into the cement paste, for example organic iodine compounds (see above). The tensio-active agent may be incorporated in one of said three components of the cement, preferably in the third component, and is preferably taken from the group of:

docusate sodium ($C_{20}H_{37}NaO_7S$), sodium lauryl sulphate ($C_{12}H_{25}NaO_4S$), stearic acid ($C_{17}H_{35}COOH$), alkyldimethyl (phenylmethyl)ammonium chloride [CAS registry number 8001-54-5], benzethonium chloride ($C_{27}H_{42}ClNO_2$), cetrimide ($C_{17}H_{38}BrN$), glycerin monooleate ($C_{21}H_{40}O_4$), polysorbate 20 ($C_{58}H_{114}O_{26}$), polysorbate 21 ($C_{26}H_{50}O_{10}$), polysorbate 40 ($C_{62}H_{122}O_{26}$), polysorbate 60 ($C_{64}H_{126}O_{26}$), polysorbate 61 ($C_{32}H_{62}O_{10}$), polysorbate 65 ($C_{100}H_{194}O_{28}$), polysorbate 80 ($C_{64}H_{124}O_{26}$), polysorbate 81 ($C_{34}H_{64}O_{11}$), polysorbate 85 ($C_{100}H_{188}O_{28}$), polysorbate 120 ($C_{64}H_{126}O_{26}$), polyvinyl alcohol (($C_2H_4O)_n$), sorbitan di-isostearate ($C_{42}H_{80}O_7$), sorbitan dioleate ($C_{42}H_{76}O_7$), sorbitan monoisostearate ($C_{24}H_{46}O_6$), sorbitan monolaurate ($C_{18}H_{34}O_6$), sorbitan monooleate ($C_{24}H_{44}O_6$), sorbitan monopalmitate ($C_{22}H_{42}O_6$), sorbitan monostearate ($C_{24}H_{46}O_6$), sorbitan sesqui-isostearate ($C_{33}H_{63}O_{6.5}$), sorbitan sesquioleate ($C_{33}H_{63}O_{6.5}$), sorbitan sesquistearate ($C_{33}H_{63}O_{6.5}$), sorbitan tri-isostearate ($C_{33}H_{63}O_{6.5}$), sorbitan trioleate ($C_{33}H_{63}O_{6.5}$), sorbitan tristearate ($C_{33}H_{63}O_{6.5}$), glyceryl monooleate ($C_{21}H_{40}O_4$), isopropyl myristate ($C_{17}H_{34}O_2$), isopropyl palmitate ($C_{19}H_{38}O_2$), lanolin [CAS registry number 8006-54-0], lanolin alcohols [CAS registry number 8027-33-6], hydrous lanolin [CAS registry number 8020-84-6], lecithin [CAS registry number 8002-43-5], medium chain triglycerides (no registry number), monoethanolamine ($C_2H_7NO$), oleic acid ($C_{17}H_{33}COOH$), polyethylene glycol monocetyl ether [CAS registry number 9004-95-9], polyethylene glycol monostearyl ether [CAS registry number 9005-00-9], polyethylene glycol monolauryl ether [CAS registry number 9002-92-0], polyethylene glycol monooleyl ether [CAS registry number 9004-98-2], polyethoxylated castor oil [CAS registry number 61791-12-6], polyoxyl 40 stearate ($C_{98}H_{196}O_{42}$), polyoxyl 50 stearate ($C_{118}H_{236}O_{52}$), triethanolamine ($C_6H_{15}NO_3$), anionic emulsifying wax [CAS registry number 8014-38-8], nonionic emulsifying wax [CAS registry number 977069-99-0], and sodium dodecyl sulphate ($NaC_{12}H_{25}SO_4$).

Quite often, bone defects are not due to a traumatic event, but to a disease, e.g. bone tumor, infection, etc . . . In these cases, it would be interesting to incorporate drugs, in particular pharmaceutically or physiologically active substances, preferably antibiotics, anti-inflammatory drugs, anti-cancer drugs, peptides, and proteins such as growth factors.

The present invention provides a method for producing a matrix of apatite as temporary bone replacement material, which method comprises the steps of:
  mixing (A) a first component comprising α-tricalcium phosphate powder particles, (B) a second component comprising calcium sulphate dihydrate (CSD), and (C) a third component comprising water, wherein (D) said hydraulic cement does not contain more calcium sulfate hemihydrate (CSH) than 10% of a total amount of said calcium suphate dihydrate (CSD) and whereby (E) said hydraulic cement does not contain a very basic component; and
  allowing said mixture to harden.

In one embodiment, the first and second components are pre-mixed and the third component is added subsequently. The invention also provides a temporary bone replacement material obtained by the method, wherein said temporary bone replacement material comprises an apatite. In one embodiment, the temporary bone replacement material further comprises CSD embedded in the apatite matrix. And, the invention also provides granules or blocks obtained by hardening the cement for in vivo implants.

The various features of novelty which characterise the invention are pointed out with particularity in the claims annexed to and forming part of this disclosure. For the better understanding of the invention, its operating advantages and specific objects attained by its use, reference should be made to the examples and descriptive matter in which are illustrated and described preferred embodiments of the invention.

EXAMPLE 1

All the cement components were pre-heated at 37° C. for one hour. 5 g α-TCP powder (specific surface area: 0.6 m$^2$/g), 0.8 g CSD powder (SSA: 0.3 m$^2$/g), 0.2 g hydroxyapatite powder (SSA: 48 m$^2$/g), and 2 ml 1.0% w/w hyaluronate solution (Mw=1000 kDa) were mixed for 60 seconds in a beaker using a spatula. Afterwards, the cement paste was placed into a pre-heated mould and left to harden at 37° C. The setting time of the cement was 9.3±1.1 min. The cement was placed in a phosphate buffer solution for 24 hours and tested mechanically. The compressive strength of the cement was 22±5 MPa.

EXAMPLE 2

All the cement components were pre-heated at 37° C. for one hour. 5 g α-TCP powder (SSA: 0.6 m$^2$/g), 3.0 g CSD powder (SSA: 0.3 m$^2$/g), 0.2 g calcium-deficient hydroxyapatite powder (SSA: 27 m$^2$/g), and 2.8 ml 1.0% w/w hyaluronate solution (Mw=1000 kDa) were mixed for 60 seconds in a beaker using a spatula. Afterwards, the cement paste was placed into a pre-heated mould and left to harden at 37° C. The setting time of the cement was 12.0±2.2 min. The cement was placed in a phosphate buffer solution for 24 hours and tested mechanically. The compressive strength of the cement was 13±3 MPa.

EXAMPLE 3

All the cement components were pre-heated at 37° C. for one hour. 5 g α-TCP powder (SSA: 0.6 m$^2$/g), 1.0 g CSD powder (SSA: 0.3 m$^2$/g), 2.0 g CSD granules (diameter 150-250 µm, 85% apparent density), 0.2 g calcium-deficient hydroxyapatite powder (SSA: 27 m$^2$/g), and 2.5 ml 1.0% w/w hyaluronate solution (Mw=1000 kDa) were mixed for 60 seconds in a beaker using a spatula. Afterwards, the cement paste was placed into a pre-heated mould and left to harden at 37° C. The setting time of the cement was 10.0±2.4 min. The cement was placed in a phosphate buffer solution for 24 hours and tested mechanically. The compressive strength of the cement was 18±4 MPa.

EXAMPLE 4

All the cement components were pre-heated at 37° C. for one hour. 5 g α-TCP powder (SSA: 0.6 m$^2$/g), 0.8 g CSD powder (SSA: 0.3 m$^2$/g), 0.2 g calcium-deficient hydroxyapatite powder (SSA: 27 m$^2$/g), and 2.5 ml of a solution containing 0.2 M Na$_2$HPO$_4$ and 1.0% w/w hyaluronate (Mw=1000 kDa) were mixed for 60 seconds in a beaker using a spatula. Afterwards, the cement paste was placed into a pre-heated mould and left to harden at 37° C. The setting time of the cement was 4.3±0.7 min. The cement was placed in a phosphate buffer solution for 24 hours and tested mechanically. The compressive strength of the cement was 28±4 MPa.

EXAMPLE 5

All the cement components were pre-heated at 37° C. for one hour. 5 g α-TCP powder (SSA: 0.6 m$^2$/g), 0.8 g CSD powder (SSA: 0.3 m$^2$/g), 2.4 ml of a solution containing 0.2M Na$_2$HPO$_4$ and 1.0% w/w hyaluronate (Mw=1000 kDa), and 0.5 ml iopamidol solution were mixed for 60 seconds in a beaker using a spatula. Afterwards, the cement paste was placed into a pre-heated mould and left to harden at 37° C. The setting time of the cement was 6.5±0.9 min. The cement was placed in a phosphate buffer solution for 24 hours and tested mechanically. The compressive strength of the cement was 21±5 MPa.

EXAMPLE 6

All the cement components were pre-heated at 37° C. for one hour. 5 g α-TCP powder (SSA: 0.6 m$^2$/g), 0.8 g CSD powder (SSA: 0.3 m$^2$/g), 0.2 g hydroxyapatite powder (SSA: 48 m$^2$/g), and 2 ml of a solution containing 2.0% w/w hyaluronate (Mw=1000 kDa) and 5% w/w gentamicin sulphate were mixed for 60 seconds in a beaker using a spatula. Afterwards, the cement paste was placed into a pre-heated mould and left to harden at 37° C. The setting time of the cement was 13.3±1.6 min. The cement was placed in a phosphate buffer solution for 24 hours and tested mechanically. The compressive strength of the cement was 19±4 MPa.

EXAMPLE 7

All the cement components were pre-heated at 37° C. for one hour. 5 g α-TCP powder (SSA: 0.6 m$^2$/g), 0.8 g CSD powder (SSA: 0.3 m$^2$/g), 0.2 g calcium-deficient hydroxyapatite powder (SSA: 27 m$^2$/g), 0.2 g K$_2$HPO$_4$ powder, and 2.8 ml of a solution containing 1.3% w/w chondroitin sulphate (Mw=1300 kDa) were mixed for 60 seconds in a beaker using a spatula. Afterwards, the cement paste was placed into a pre-heated mould and left to harden at 37° C. The setting time of the cement was 5.9±0.7 min. The cement was placed in a phosphate buffer solution for 24 hours and tested mechanically. The compressive strength of the cement was 25±5 MPa.

EXAMPLE 8

All the cement components were pre-heated at 37° C. for one hour. 5 g α-TCP powder (SSA: 2.5 m$^2$/g), 0.8 g CSD powder (SSA: 0.3 m$^2$/g), 0.2 g calcium-deficient hydroxyapatite powder (SSA: 27 m$^2$/g), 0.2 g K$_2$HPO$_4$ powder, and 2.8 ml of a solution containing 1.3% w/w chondroitin sulphate (Mw=1300 kDa) were mixed for 60 seconds in a beaker using a spatula. Afterwards, the cement paste was placed into a pre-heated mould and left to harden at 37° C. The setting time of the cement was 5.9±0.7 min. The cement was placed in a phosphate buffer solution for 24 hours and tested mechanically. The compressive strength of the cement was 25±5 MPa.

EXAMPLE 9 x g a-TCP(SSA=2.4 m2/g) were mixed with 0.37 g CSD (0.8 m2/g) and (4-0.37-x)g of calcium carbonate (CaCO3; 1.5 m2/g) where x varied between 3.20 and 3.63 g. The powder was then mixed with 1.5-1.7 mL of a potassium phosphate solution (0.2 M KH2PO4) and the resulting paste was kneaded for 60 seconds. Afterwards, the paste was placed into a syringe whose tip had been previously cut off and its setting time was determined. The cement setting time increased gradually with an increase in CaCO3 content. The x-ray diffraction analysis (XRD) of the cement after two days of incubation at 37 C showed that the setting reaction was strongly slowed by the addition of CaCO3. However, the specific surface area of the cement was strongly increased (+50% with 5% CaCO3).

EXAMPLE 10

The following pre-sterilized components, i.e. 7.26 g a-TCP (SSA=2.4 m2/g), 0.74 g CSD (0.8 m2/g), 0.10 g NaH2PO4. 2.0 mL of iopamidol (organic iodine solution) and 1.2 mL of a 4% sodium hyaluronate solution, were mixed together in a sterile and closed mixer. After 30 seconds of thorough mixing, the paste was injected from the mixer into two 2 mL syringes. The paste present in the syringes was then injected into the osteoporotic vertebrae (BMD=−3.5) of a corpse. The x-ray analysis of the vertebra showed a very good radiographical contrast, as well as a perfect cement distribution (spherical distribution).

EXAMPLE 11

9 g a-TCP (SSA=2.4 m2/g) were mixed with 0.9 g CSD (0.8 m2/g), 2.1 g of calcium carbonate powder (CaCO3; 1.5 m2/g; average diameter in number: 1.9 m), and 4.5 mL of a 0.1M MgSO4. 0.1M Na2HPO4, and 0.05 M Na2H2P2O7 solution. After 2 minutes of mixing, the paste placed into a cylindrical form, and vibrated with a vibrator to eliminate air bubbles. The top of the form was then covered with a wet piece of cloth. Thirty minutes after setting (Setting time=47 min+/−5 min), the block was unmoulded and placed in 10 mL of phosphate buffer solution (pH 7.4, 0.15M) at 37 C for 5 days. After that time, the block was dried at 60 C for 3 days and then ground (with a mortar and a pestle) and sieved. The granules in the range of 0.125 mm to 2.8 mm were collected for further use in an in vivo application. All operations were performed in aseptic conditions with sterile components.

EXAMPLE 12

9 g a-TCP (SSA=2.4 m2/g) were mixed with 0.9 g CSD (0.8 m2/g), 2.1 g of calcium carbonate powder (CaCO3; 1.5 m2/g; average diameter in number: 1.9 m), 4 g of maltose crystals (0.2 mm in diameter), and 4.5 mL of a 0.1M MgSO4, 0.1M Na2HPO4, and 0.05 M Na2H2P2O7 solution. After 2 minutes of mixing, the paste placed into a cylindrical form, and vibrated rapidly with a vibrator to eliminate air bubbles. The top of the form was then covered with a wet piece of cloth. Thirty minutes after setting (Setting time=47 min+/−5 min), the block was unmoulded and placed in 50 mL of phosphate buffer solution (pH 7.4, 0.15M) at 37 C for 5 days. After that time, the block was dried at 60° C. for 3 days for further use in an in vivo application. All operations were performed in aseptic conditions with sterile components.

The invention claimed is:

1. A hydraulic cement based on calcium phosphate for surgical use comprising:
    A) a first component comprising α-tricalcium phosphate powder particles (TCP);
    B) a second component comprising calcium sulfate dihydrate (CSD); and
    C) a third component comprising water;
    wherein
    D) the cement does not contain more calcium sulfate hemihydrate (CSH) than 10% of a total amount of said calcium sulfate dihydrate (CSD);
    E) the cement does not contain tetracalcium phosphate (TTCP); and
    F) at least one of the components comprises an apatite powder as a setting accelerator.

2. The cement according to claim 1, wherein the cement does not contain more calcium sulfate hemihydrate (CSH) than 2% of the total amount of the calcium sulfate dihydrate (CSD).

3. The cement according to claim 2, wherein essentially no calcium sulfate hemihydrate (CSH) is detectable in the cement.

4. The cement according to claim 1, wherein the powder particles of said first component have an average diameter less than 20 μm.

5. The cement according to claim 1, wherein at least one of the three cement components comprises a setting regulator.

6. The cement according to claim 1, wherein the first or second component comprises a setting accelerator.

7. The cement according to claim 1, wherein the setting accelerator is one of a calcium-deficient hydroxyapatite and a hydroxyapatite powder.

8. The cement according to claim 1, wherein the setting accelerator is a water-soluble phosphate salt selected from the group consisting of $Na_2HPO_4$, $NaH_2PO_4$, $K_2HPO_4$, $KH_2PO_4$ and $NH_4H_2PO_4$.

9. The cement according to claim 1, wherein the third component comprises a setting accelerator.

10. The cement according to claim 9, wherein the setting accelerator is a dissolved phosphate salt selected from the group consisting of $Na_2HPO_4$, $NaH_2PO_4$, $K_2HPO_4$, $KH_2PO_4$ and $NH_4H_2PO_4$.

11. The cement according to claim 5, wherein the setting regulator is a setting retarder.

12. The cement according to claim 1, wherein the first or second component comprises a setting retarder.

13. The cement according to claim 12, wherein the setting retarder is selected from the group consisting of citrate, pyrophosphate, carbonate and magnesium ions.

14. The cement according to claim 1, wherein a setting time of a cement paste obtained by mixing said three components at 37° C. is between 1 and 20 minutes.

15. The cement according to claim 14, wherein the setting time of the cement paste at 37° C. is between 2 and 15 minutes.

16. The cement according to claim 15, wherein the setting time of the cement paste at 37° C. is between 5 and 12 minutes.

17. The cement according to claim 1, wherein a Ca/P molar ratio of a cement paste obtained by mixing said three components is greater than 1.5.

18. The cement according to claim 17, wherein the Ca/P molar ratio of the cement is equal to 1.667.

19. The cement according to claim 17, wherein the Ca/P molar ratio of the cement is greater than 1.667.

20. The cement according to claim 17, wherein the Ca/P molar ratio of the cement is greater than or equal to 2.0.

21. The cement according to claim 1, wherein one of the components contain a radiological contrasting agent.

22. The cement according to claim 21, wherein the radiological contrasting agent is a liquid compound.

23. The cement according to claim 22, wherein the radiological contrasting agent is an organic iodine compound selected from the group consisting of iopamidol ($C_{17}H_{22}I_3N_3O_8$), iohexol ($C_{19}H_{26}I_3N_3O_9$), and iotrolan ($C_{37}H_{48}I_6N_6O_{18}$).

24. The cement according to claim 1, wherein one of said three components comprises an additive to control the cement rheology.

25. The cement according claim 24, wherein the third component comprises an additive to control the cement rheology.

26. The cement according to claim 24, wherein the additive used to control the cement rheology is selected from the group consisting of polysaccharide derivatives comprising hyaluronic acid or salt, chondroitin sulfate, dermantan sulfate, heparan sulfate, heparin, dextran, alginate, keratan sulfate, hydroxypropylmethyl cellulose, chitosan, xanthan gum, guar gum, and carrageenan.

27. The cement according to claim 24, wherein the additive used to control the cement rheology is hyaluronic acid and/or hyaluronic salt.

28. The cement according to claim 24, wherein a concentration of the additive used to control the cement rheology is larger than 1 weight percent of the third component.

29. The cement according to claim 1, wherein a volume VL of the third component is in the range of $0.5\ VT \leq VL \leq 10.0\ VT$ where VT is total powder volume of the first and second component.

30. The cement according to claim 29, wherein the volume VL of the third component is in the range of $1.0\ VT \leq VL \leq 2.5\ VT$ where VT is the total powder volume of the first and second component.

31. The cement according to claim 1, wherein the first or second component of the cement may further comprise bioresorbable or biodegradable granules whose diameter are at least two times larger than the average diameter of said powder particles of said first component.

32. The cement according to claim 31, wherein the granules have an average diameter in the range of 100 μm to 500 μm.

33. The cement according to claim 32, wherein the granules have an average diameter in the range of 200 μm to 350 μm.

34. The cement according to claim 31, wherein the granules are made of calcium phosphate, CSD, polymer or bioglass.

35. The cement according to claim 1, wherein said first and second component is in the form of particles having an average diameter larger than 0.1 μm.

36. The cement according to claim 1, wherein one or more of said three components comprises pharmaceutically or physiologically active substances selected from the group consisting of antibiotics, anti-inflammatory drugs, drugs against osteoporosis, anti-cancer drugs, peptides, and proteins.

37. The cement according to claim 1, wherein the one of said three components comprises a tensio-active agent selected from the group consisting of: docusate sodium ($C_{20}H_{37}NaO_7S$), sodium lauryl sulfate ($C_{12}H_{25}NaO_4S$), stearic acid ($C_{17}H_{35}COOH$), alkyldimethyl(phenylmethyl)-ammonium chloride [CAS registry number 8001-54-5], benzethonium chloride ($C_{27}H_{42}ClNO_2$), cetrimide ($C_{17}H_{38}BrN$), glycerin monooleate ($C_{21}H_{40}O_4$), polysorbate 20 ($C_{58}H_{114}O_{26}$), polysorbate 21 ($C_{26}H_{50}O_{10}$), polysorbate 40 ($C_{62}H_{122}O_{26}$), polysorbate 60 ($C_{64}H_{126}O_{26}$), polysorbate 61 ($C_{32}H_{62}O_{10}$), polysorbate 65 ($C_{100}H_{194}O_{28}$), polysorbate 80 ($C_{64}H_{124}O_{26}$), polysorbate 81 ($C_{34}H_{64}O_{11}$), polysorbate 85 ($C_{100}H_{188}O_{28}$), polysorbate 120 ($C_{64}H_{126}O_{26}$), polyvinyl alcohol ($((C_2H_4O)_n)$), sorbitan di-isostearate ($C_{42}H_{80}O_7$), sorbitan dioleate ($C_{42}H_{76}O_7$), sorbitan monoisostearate ($C_{24}H_{46}O_6$), sorbitan monolaurate ($C_{18}H_{34}O_6$), sorbitan monooleate ($C_{24}H_{44}O_6$), sorbitan monopalmitate ($C_{22}H_{42}O_6$), sorbitan monostearate ($C_{24}H_{46}O_6$), sorbitan sesqui-isostearate ($C_{33}H_{63}O_{6.5}$), sorbitan sesquioleate ($C_{33}H_{63}O_{6.5}$), sorbitan sesquistearate ($C_{33}H_{63}O_{6.5}$), sorbitan tri-isostearate ($C_{33}H_{63}O_{6.5}$), sorbitan trioleate ($C_{33}H_{63}O_{6.5}$), sorbitan tristearate ($C_{33}H_{63}O_{6.5}$), glyceryl monooleate ($C_{21}H_{40}O_4$), isopropyl myristate ($C_{17}H_{34}O_2$), isopropyl palmitate ($C_{19}H_{38}O_2$), lanolin [CAS registry number 8006-54-0], lanolin alcohols [CAS registry number 8027-33-6], hydrous lanolin [CAS registry number 8020-84-6], lecithin [CAS registry number 8002-43-5], medium chain triglycerides (no registry number), monoethanolamine ($C_2H_7NO$), oleic acid ($C_{17}H_{33}COOH$), polyethylene glycol monocetyl ether [CAS registry number 9004-95-9], polyethylene glycol monostearyl ether [CAS registry number 9005-00-9], polyethylene glycol monolauryl ether [CAS registry number 9002-92-0], polyethylene glycol monooleyl ether [CAS registry number 9004-98-2], polyethoxylated castor oil [CAS registry number 61791-12-6], polyoxyl 40 stearate ($C_{98}H_{196}O_{42}$), polyoxyl 50 stearate ($C_{118}H_{236}O_{52}$), triethanolamine ($C_6H_{15}NO_3$), anionic emulsifying wax [CAS registry number 8014-38-8], nonionic emulsifying wax [CAS registry number 977069-99-0], and sodium dodecyl sulfate ($NaC_{12}H_{25}SO_4$).

38. The cement according to claim 1, wherein the specific surface area (SSA) of the powder particles of said first component is in the range of 0.05 to 10.000 $m^2/g$.

39. The cement according to claim 38, wherein the specific surface area (SSA) of the first component is in the range of 1 to 2 $m^2/g$.

40. The cement according to claim 1, wherein a viscosity of the cement is larger than 1 Pa·s at a shear rate of $400s^{-1}$, one minute after the start of cement mixing.

41. The cement according to claim 40, wherein the cement viscosity of the cement is larger than 10 Pa·s at a shear rate of $400s^{-1}$, one minute after the start of cement mixing.

42. The cement according to claim 1, wherein the cement consists of a powder/liquid formulation to be mixed, whereby
  a) a powder comprises said first and second component; and
  b) a liquid comprises the third component.

43. The cement according to claim 1, wherein the cement consists of the following parts:
  c) a powder comprising said first and second component
  d) a first viscous solution comprising said third component; and
  e) a second solution comprising a contrasting agent.

44. The cement according to claim 42, wherein component a) additionally comprises water-soluble phosphate salts and component b) comprises a polymer.

45. The cement according to claim 1, wherein a setting time of the mixture of said three components is between 2 to 15 minutes.

46. A method for producing a matrix of apatite as temporary bone replacement material, comprising the steps of mixing said three components of claim 1 and allowing said mixture to harden.

47. Method according to claim 46, wherein the first and second component are pre-mixed and the third component is added subsequently.

48. A temporary bone replacement material obtained by the method according to claim 46, wherein said temporary bone replacement material comprises an apatite.

49. The temporary bone replacement material according to claim 48, wherein said temporary bone replacement material comprises CSD embedded in said apatite matrix.

50. Granules or blocks obtained by hardening the cement according to claim 1 for in vivo implants.

51. A hydraulic cement based on calcium phosphate for surgical use comprising:
  a first component comprising α-tricalcium phosphate powder particles (TCP) having an average diameter less than 20 μm;

a second component comprising calcium sulfate dihydrate (CSD); and a third component comprising water;

wherein:

at least one of the first, second or third components comprises an apatite powder as a setting accelerator;

at least one of the first, second or third components comprises an additive to control the cement rheology; and the cement does not contain more calcium sulfate hemihydrate (CSH) than 10% of a total amount of said calcium sulfate dihydrate (CSD).

* * * * *